US00PP11354P

United States Patent [19]

Turc

[11] Patent Number: Plant 11,354

[45] Date of Patent: Apr. 18, 2000

[54] ALSTROEMERIA PLANT NAMED 'LOIRIEON'

[75] Inventor: Jean Pierre Turc, Mazé, France

[73] Assignee: Selection New Plant SARL, Le Luc, France

[21] Appl. No.: 09/116,952

[22] Filed: Jul. 17, 1998

[51] Int. Cl.[7] ..... A01H 5/00

[52] U.S. Cl. ..... Plt./309

[58] Field of Search ..... Plt./309

*Primary Examiner*—Howard J. Locker

*Attorney, Agent, or Firm*—Burns, Doane, Swecker & Mathis, L.L.P.

[57] ABSTRACT

A new and distinct variety of Alstroemeria plant of very tall height is provided which abundantly forms on a substantially continuous basis attractive large salmon pink blended with yellow flowers (as illustrated). The flowers are borne on peduncles as an umbel. The plant propagates well by the division of roots. The plant can be grown as distinctive ornamentation under mild temperature conditions.

1 Drawing Sheet

SUMMARY OF THE INVENTION

The new variety of Alstroemeria was created by artificial pollination wherein two parents were crossed which previously had been studied in the hope that they would contribute the desired characteristics. The female parent (i.e., the seed parent) of the new variety was the 'Turcalva' variety (non-patented in the United States). The 'Turcalva' variety is marketed in Europe under the VALERIE trademark. The male parent (i.e., the pollen parent) of the new variety was the 'Yellow King' variety (non-patented in the United States). The parentage of the new variety can be summarized as follows:

'Turcalva'×'Yellow King'.

The seeds resulting from the above pollination were sown and small plants were obtained which were physically and biologically different from each other. Selective study resulted in the identification of a single plant of the new variety.

It was found that the new Alstroemeria plant of the present invention possesses the following combination of characteristics:

(a) forms in abundance attractive large salmon pink blended with yellow flowers having prominent streaks of orange-red which are borne on peduncles as an umbel,
(b) exhibits a very tall plant height,
(c) propagates well by the division of roots, and
(d) is particularly suited for growing as a distinctive ornamental plant under mild temperature conditions.

The salmon pink blended with yellow flowers (as illustrated) of the new variety of the present invention can be readily distinguished from the bright red flowers of the 'Loiricha' variety (U.S. Plant Pat. No. 10,312), and the pink flowers of the 'Loiridau' variety (U.S. Plant patent application No. 09/116,953, filed concurrently herewith).

The new variety well meets the needs of the horticultural industry. It is particularly well-suited for use as attractive ornamentation in the landscape or for growing as a decorative pot plant.

The new variety has been found to undergo asexual propagation in France by the separation or splitting of roots. Asexual propagation by the above-mentioned methods as performed in France has shown that the characteristics of the new variety are strictly transmissible from one generation to another.

The new variety has been named the 'Loirieon' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The Alstroemeria plants of the new variety were sixteen months of age and were observed during November while growing in greenhouses at Mazé, Maine et Loire, France. Size information in centimeters is provided at the bottom of the photograph.

DETAILED DESCRIPTION

Figures 1, 2, 3, 4, 5, 6, 7, 8, 9, 10, 11, 12, 13, 14:
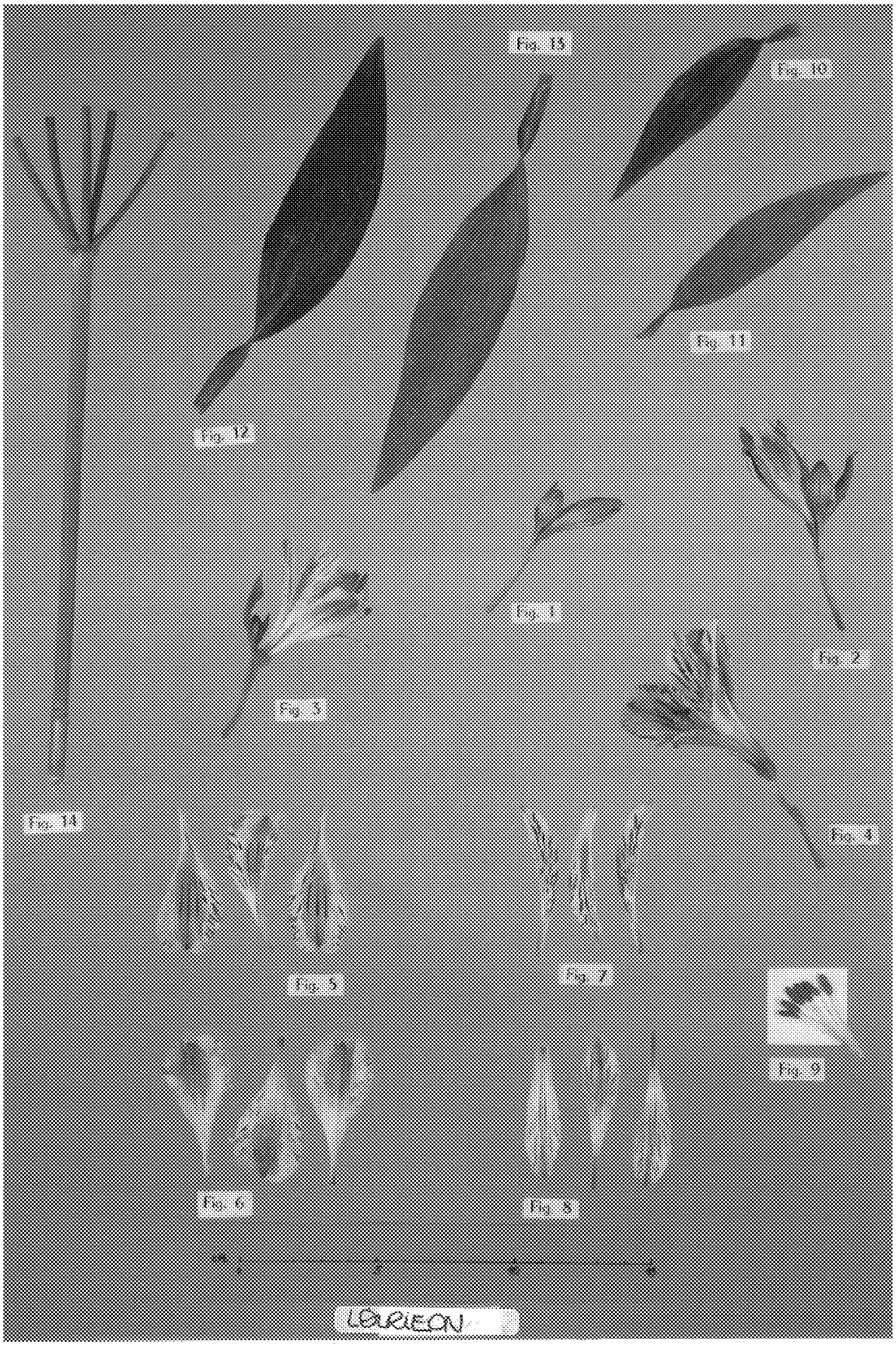
FIG. 1 illustrates a specimen of a floral bud.
FIG. 2 illustrates a specimen of a floral bud in the course of opening.
FIG. 3 illustrates a specimen of a flower in the course of opening.
FIG. 4 illustrates a specimen of an open flower.
FIG. 5 illustrates specimens of external floral petals — plan view — obverse.
FIG. 6 illustrates specimens of external floral petals — plan view — reverse.
FIG. 7 illustrates specimens of central floral petals — plan view — obverse.
FIG. 8 illustrates specimens of central floral petals — plan view — reverse.
FIG. 9 illustrates specimens of stamens.
FIG. 10 illustrates a specimen of a bract — plan view — obverse.
FIG. 11 illustrates a specimen of a bract — plan view — reverse.
FIG. 12 illustrates a specimen of a leaf — plan view — obverse.
FIG. 13 illustrates a specimen of a leaf — plan view — reverse.
FIG. 14 illustrates a specimen of a stem.

The chart used in the identification of the colors is that of The Royal Horticultural Society (R.H.S. Colour Chart). Color terminology is used in some instances to indicate the corresponding colors in more common terms that are to be accorded their ordinary dictionary significance. The description is based on the observation of sixteen month-old specimens of the new variety during May while growing in greenhouses at Mazé, Maine et Loire, France.

Origin: Artificial pollination.

Parentage:

*Female.*—'Turcalva' which is marketed under the VALERIE trademark in Europe.

*Male.*—'Yellow King'.

Classification: Alstreomeria Hybrid.

Plant:

*Form.*—Herbaceous perennial.

*Height.*—Size: very tall, approximately 1.5 to 1.9 m. on average.

*Habit.*—Fast growing with vigorous upright stems of good strength.

*Rhizome color.*—White, near White Group 155D.

*Rhizome size.*—Variable with the growing season which occurs from spring to autumn. During June a typical length is approximately 15 to 20 cm. The growth is substantially horizontal.

Foliage:

*Leaf shaped.*—Elliptical.

*Leaf size.*—Approximately 12.5 cm. in length and approximately 3 cm. in width.

*Texture.*—Glossy on upper surface.

*Margin.*—Smooth.

*Color.*—Adult foliage is medium green, Yellow-Green Group 137A on the upper surface, and near Green Group 137B on the under surface.

*Number.*—Approximately 18 to 23 on average.

Inflorescence:

*Main stem length.*—Approximately 0.7 to 1.1 m.

*Main stem color.*—Green Group 143C.

*Peduncle length.*—Commonly approximately 9 to 11 cm.

*Peduncle disposition.*—Erect.

*Peduncle color.*—Green Group 143C.

*Buds.*—Shape: oblong and pear-shaped. Size: approximately 4 to 4.5 cm. in length, and approximately 1 to 1.5 cm. in diameter.

*Color.*—Yellow-Green Group 144B.

*Blooming habit.*—Continuous with no substantial interruption.

*Blooms.*—Size: large in an umbel. Diameter: approximately 6 cm. Depth: approximately 4 cm. Borne: singly on a stem, and approximately 4 to 5 blooms on average per umbel. Umbel size: commonly approximately 12 cm. on average. Form: cup-shaped. Number of tepals: three internal tepals and three external tepals. Arrangement: generally two concentric circles of three tepals each. Texture: soft. Appearance: satiny. Color (in course of opening): Central tepals (obverse): at the tip and base near Red Group 51C with streaks of Greyed-Purple Group 187A, and at the central portion Yellow Group 2A with streaks of Greyed-Purple Group 187A. The coloration tends to be darker on the upper tepal surface. Central tepals (reverse): at the tip and base near Red Group 51C, and at the central portion Yellow Group 2B. Commonly the streaks tend to be somewhat less pronounced on the reverse. External tepals (obverse): on the margin to a width of approximately 1 cm. near Red Group 37B and concentrated toward the center is a sometimes oval-shaped area that is suffused with Red Group 51B, and beyond this suffusion is Yellow Group 5B which is more or less suffused with Red Group 37B towards the margins. Streaks and yellow coloration similar to that of the inner tepals are present. Such streaks tend to be larger when centrally located and are smaller towards the margins. The coloration tends to be slightly darker on the upper tepal surface. External tepals (reverse): the central portion is Orange-Red Group 34B, and the margin is Red Group 51C to a width of approximately 1 cm. with Yellow Group 8C at the center. There commonly are streaks of Greyed-Purple Group 187A and visible veinlets. Color (after full bloom): whitening tends to occur. Internal tepal shape: elliptic with smooth margin. External tepal shape: cordate and oblong with smooth margin. Lasting quality: approximately 4 to 5 weeks on the plant, and approximately 3 weeks when the blossoms are cut and are placed in a vase. Fragrance: none. Stamens: commonly six in number with one being arranged opposite each tepal. Anthers: before dehiscence greenish-brown in coloration and after dehiscence dark greenish-brown in coloration, and commonly approximately 9 mm. in length. Filaments: pink-violet in coloration and approximately 3 to 4 cm. in length. Pollen: greenish-gray in coloration. Pistils: commonly one. Styles: pink-violet in coloration and approximately 2 to 2.5 cm. in length. Stigmas: yellowish in coloration with claret red spots. Fruit: greenish-brown in coloration at maturity, rounded, and commonly infertile.

Development:

*Propagation.*—Propagates well through the division of roots.

*Resistance to diseases.*—Good with respect to traditional disease under greenhouse growing conditions.

*Resistance to frost.*—None with the best culture conditions being exhibited above 20° C.

I claim:

1. A new and distinct variety of Alstroemeria plant characterized by the following combination of characteristics:

(a) forms in abundance attractive large salmon pink blended with yellow flowers having prominent streaks of orange-red which are borne on peduncles as an umbel;
(b) exhibits a very tall plant height;
(c) propagates well by the division of roots; and
(d) is particularly suited for growing as a distinctive ornamental plant under mild temperature conditions;

substantially as herein shown and described.

* * * * *

LOURIEON